(12) United States Patent
Takagaki et al.

(10) Patent No.: US 7,863,466 B2
(45) Date of Patent: Jan. 4, 2011

(54) METHOD OF PRODUCING PROANTHOCYANIDIN-CONTAINING MATERIAL

(75) Inventors: Kinya Takagaki, Fukuoka (JP); Gotaro Yamaguchi, Fukuoka (JP)

(73) Assignee: Toyo Shinyaku Co., Ltd., Fukuoka (JP)

( * ) Notice: Subject to any disclaimer, the term of this patent is extended or adjusted under 35 U.S.C. 154(b) by 595 days.

(21) Appl. No.: 11/910,984

(22) PCT Filed: Apr. 13, 2006

(86) PCT No.: PCT/JP2006/308265

§ 371 (c)(1),
(2), (4) Date: Oct. 10, 2007

(87) PCT Pub. No.: WO2006/112496

PCT Pub. Date: Oct. 26, 2006

(65) Prior Publication Data

US 2009/0124818 A1      May 14, 2009

(30) Foreign Application Priority Data

Apr. 15, 2005    (JP)  ................. PCT/JP2005/007669

(51) Int. Cl.
    *C07D 311/62*      (2006.01)
(52) U.S. Cl. ..................................................... 549/399
(58) Field of Classification Search .................. 549/399
See application file for complete search history.

(56) References Cited

U.S. PATENT DOCUMENTS

2001/0036487 A1    11/2001    Takahasi et al. ............. 424/732

FOREIGN PATENT DOCUMENTS

| | | |
|---|---|---|
| JP | 59196884 | 11/1984 |
| JP | 04190774 | 7/1992 |
| JP | 05279264 | 10/1993 |
| JP | 06056689 | 3/1994 |
| JP | 06247959 | 9/1994 |
| JP | 09315985 | 12/1997 |
| JP | 09315992 | 12/1997 |
| JP | 10218769 | 8/1998 |
| JP | 11080148 | 3/1999 |
| JP | 2001131027 | 5/2001 |
| JP | 2002097187 | 4/2002 |
| JP | 2004315476 | 11/2004 |
| JP | 2004359640 | 12/2004 |
| JP | 200523032 | 1/2005 |
| JP | 200547818 | 2/2005 |
| WO | 03/090770 | 11/2003 |

OTHER PUBLICATIONS

Porter, New Zealand Journal of Science, vol. 17, p. 213-218 (1974).*
International Search Report, Application No. PCT/JP2006/308265.
Eberhard Scholz et al.; "Proanthocyanidins from *Krameria triandra* Root"; *Planta Medica*, 55 (1989), pp. 379-384.

* cited by examiner

*Primary Examiner*—Bernard Dentz
(74) *Attorney, Agent, or Firm*—Renner, Otto, Boisselle & Sklar, LLP

(57) ABSTRACT

The method for producing proanthocyanidin-containing product of the present invention comprises the steps of providing a pine bark as a starting material, extracting the pine bark with at least one of water and an organic solvent, and treating the resultant extract with a synthetic resin adsorbent, wherein the pine bark has characteristics in that at least 7 wt % of solid material in terms of dry weight is obtained from a pine bark extract that is obtained by adding 10 parts by volume of an aqueous ethanol solution containing ethanol in the range of 50 to 80 volume % to one part by weight of the pine bark, and performing extraction at 80 to 85° C. for one hour. It is possible to conveniently and efficiently obtain proanthocyanidin-containing product that contains at least 10 wt % of OPCs.

1 Claim, No Drawings

METHOD OF PRODUCING PROANTHOCYANIDIN-CONTAINING MATERIAL

TECHNICAL FIELD

The present invention relates to a method for efficiently producing a proanthocyanidin-containing product that contains a large amount of highly bioactive OPCs.

BACKGROUND ART

Proanthocyanidins are tannins that are present in various plants. Proanthocyanidins are a group of compounds that are condensation or polymerization products (hereinafter, referred to as "condensation products") and have flavan-3-ol and/or flavan-3,4-diol as a constituent unit. When these compounds are subjected to acid treatment, anthocyanidins such as cyanidin, delphinidin, and pelargonidin are produced. Therefore, these compounds are designated as proanthocyanidins.

Proanthocyanidins, which are one type of polyphenol, are potent antioxidants produced by plants, and are contained concentratedly in portions of plant leaves, bark, or skin or seeds of fruits. More specifically, proanthocyanidins are contained in, for example, the seeds of grape; the bark of pine; the skin of peanut; the leaves of ginkgo; the fruit of locust; and the fruit of cowberry. Moreover, it is known that proanthocyanidins are also contained in cola nuts in West Africa; the roots of Rathania in Peru; and Japanese green tea. Proanthocyanidins cannot be produced in the human body.

In recent years, it has been reported that among the proanthocyanidins, proanthocyanidins having a low degree of polymerization, and in particular condensation products having a degree of polymerization of 2 to 4 (dimer to tetramer), have excellent bioactivity. The condensation products having a degree of polymerization of 2 to 4 are generally referred to as oligomeric proanthocyanidins (OPCs).

Such proanthocyanidins are obtained by extracting from plants. As the extraction solvent, water; an organic solvent such as methanol, ethanol, acetone, hexane, and ethyl acetate; or a mixture thereof, is generally used (Japanese Laid-Open Patent Publication No. 11-80148). However, when simply performing an extraction with a solvent, the purity of the resultant extract is low and also the amount of proanthocyanidins that can be recovered is small. Therefore, in order to use the extract as raw materials for health food products, cosmetics, and drugs, it is necessary to increase the purity. Thus, additional processes such as concentration and purification are required, which increases the cost and time.

The following methods have been proposed as methods for recovering polyphenols containing proanthocyanidins. For example, Japanese Laid-Open Patent Publication Nos. 5-279264 and 6-56689 describe a process of adsorbing polyphenols to a chitin substrate and that the chitin substrate to which the polyphenols are adsorbed is utilized as a polyphenol product. Japanese Laid-Open Patent Publication No. 2002-97187 describes a method for recovering free polyphenols that comprises adding ascorbic acid and an alkali metal or a salt thereof to a plant extract liquid in order to adjust the pH in the range of 6 to 11, thereby precipitating a metal salt of polyphenols, recovering the metal salt, desalting the metal salt with an ion exchange resin or the like, and recovering the resultant free polyphenols.

However, most of the proanthocyanidins that can be obtained by any one of the above-described methods have a high degree of polymerization, and the content of OPCs (i.e., condensation products having a degree of polymerization of 2 to 4) that have excellent effects is very low.

Examples of methods for extracting OPCs from plants and/or synthesizing OPCs are disclosed in Japanese Laid-Open Patent Publication Nos. 4-190774, 10-218769, and 2001-131027; and Eberhard Scholz et al., "Proanthocyanidins from Krameria triandra Root", Planta Medica, 55 (1989), pp. 379-384. However, in these extraction methods, an extract liquid of a plant is brought into contact with an adsorbent, the adsorbed material is eluted, and specific fractions are collected, and thereafter the same process is repeated using the collected fractions. Without repeating the process, an OPC-containing product having a high OPC content cannot be obtained, which is not efficient. The synthesizing methods also include a lot of steps, which causes problems of high cost and long time. Furthermore, the synthesizing methods also have a problem of liquid waste disposal.

Further, the inventors of the present application have disclosed that proanthocyanidin-containing product is obtained by the process of bringing an extract or juice of a plant into contact with a substrate made of chitin, chitosan, or a derivate thereof, recovering the resultant extract or juice containing materials that have not been adsorbed, and treating the resultant extract or juice with a synthetic resin adsorbent (WO03/090770); and that a pine bark extract with an increased proanthocyanidin content is obtained by the process of treating a pine bark extract with an adsorbent resin (Diaion HP-20, etc.) (Japanese Laid-Open Patent Publication No. 2005-47818).

However, there is a demand for a simple method for purifying proanthocyanidins containing a large amount of OPCs in addition to the above-mentioned methods.

DISCLOSURE OF THE INVENTION

The inventors of the present invention conducted in-depth studies on a method for efficiently obtaining proanthocyanidin-containing product that contains OPCs having excellent bioactivity, at a high ratio. As a result, they found that it is possible to simply and efficiently obtain proanthocyanidin-containing product that contains at least 10 wt % of OPCs by employing the steps of providing a pine bark as a starting material, extracting the pine bark with at least one of water and an organic solvent, and treating the resultant extract with a synthetic resin adsorbent, wherein the pine bark has characteristics in that at least 7 wt % of solid material in terms of dry weight is obtained from a pine bark extract that is obtained by adding 10 parts by volume of an aqueous ethanol solution containing ethanol in the range of 50 to 80 volume % to one part by weight of the pine bark, and performing extraction at 80 to 85° C. for one hour, and thus the present invention was achieved.

The present invention provides a method for producing proanthocyanidin-containing product that comprises at least 10 wt % of OPCs, comprising the steps of: providing a pine bark as a starting material, extracting the pine bark with at least one of water and an organic solvent, and treating the resultant extract with a synthetic resin adsorbent, wherein the pine bark has characteristics in that at least 7 wt % of solid material in terms of dry weight is obtained from a pine bark extract that is obtained by adding 10 parts by volume of an aqueous ethanol solution containing ethanol in the range of 50 to 80 volume % to one part by weight of the pine bark, and performing extraction at 80 to 85° C. for one hour.

In one embodiment, the synthetic resin adsorbent is at least one selected from the group consisting of aromatic resins, (meth)acrylic acid resins, and (meth)acrylate resins.

In one embodiment, the above-mentioned step of treating the extract with the synthetic resin adsorbent comprises, bringing the extract and the synthetic resin adsorbent into contact with each other, eluting the adsorbed material from the adsorbent with an aqueous solution containing alcohol in a ratio of 10 to 30 volume %, and recovering the resultant eluate.

BEST MODE FOR CARRYING OUT THE INVENTION

The method for producing proanthocyanidin-containing product of the present invention comprises the steps of providing a pine bark as a starting material, extracting the pine bark with at least one of water and an organic solvent (hereinafter, this step is referred to as "extraction step"), and treating the resultant extract with a synthetic resin adsorbent (hereinafter, this step is referred to as "synthetic resin adsorbent treatment step"), wherein the pine bark has characteristics in that at least 7 wt % of solid material in terms of dry weight is obtained from a pine bark extract that is obtained by adding 10 parts by volume of an aqueous ethanol solution containing ethanol in the range of 50 to 80 volume % to one part by weight of the pine bark, and performing extraction at 80 to 85° C. for one hour. In this specification, first, the pine bark that can be used in the present invention will be described, and then the extraction process and the synthetic resin adsorbent treatment process will be described. Next, proanthocyanidin-containing product that is obtained will be described.

(Pine Bark Used in the Present Invention)

The pine bark that is used in the present invention has characteristics in that at least 7 wt %, preferably at least 13 wt %, and more preferably 13 wt % to 30 wt % of solid material in terms of dry weight is obtained from a pine bark extract that is obtained by adding 10 parts by volume of an aqueous ethanol solution containing ethanol in the range of 50 to 80 volume % to one part by weight of the pine bark, and performing extraction at 80 to 85° C. for one hour. Hereinafter, the above-mentioned solid material is referred to as the aqueous ethanol soluble components. By using pine bark that contains the aqueous ethanol soluble components in a ratio of at least 7 wt %, it becomes possible to efficiently obtain proanthocyanidin-containing product that contains at least 10 wt % of OPCs with only one process of column chromatography. When an aqueous solution whose ethanol content is outside the range of 50 to 80 volume % is used, it is not possible to obtain the desired proanthocyanidin-containing product that contains at least 10 wt % of OPCs, even though the aqueous ethanol soluble components are at least 7 wt %. One of the features of the present invention is that it is possible to readily obtain proanthocyanidin-containing product that contains at least 10 wt % of OPCs by screening and selecting the pine bark in advance, wherein the screening employs the above-described extraction conditions.

The content of the aqueous ethanol soluble components in the pine bark can, for example, be measured as follows. First, 100 g (dry weight) of pine bark is powdered by using a cutter, slicer, mill or the like; or using a pulverizer such as a mixer, juicer, blender, or masscolloider. Then, 1 L of an aqueous ethanol solution containing ethanol in the range of 50 to 80 volume % is added to 100 g of this powder, and heated under reflux at 80 to 85° C. for one hour for extraction. After the extraction, a separation operation such as centrifugation or filtration is performed, and the insoluble components are removed, yielding an extract liquid. It is preferable to perform a re-extraction process in which the above extraction operation and separation operation are repeated at least once on the extraction residue because this allows the aqueous ethanol soluble components in the pine bark to be measured accurately. The extraction liquid that is obtained is freeze dried or vacuum concentrated to dryness, and the weight of the resultant dried product is measured. The ratio of the weight of the resultant dried product to the dry weight of the pine bark before extraction is calculated to find the content of the aqueous ethanol soluble components.

(Extraction Process)

In the method of the present invention, first, pine bark containing at least 7 wt % of the aqueous ethanol soluble components is extracted with at least one of water and an organic solvent to obtain a pine bark extract.

The extraction is carried out at a predetermined temperature that is maintained as necessary. In view of the extraction efficiency, it is preferable to increase the surface area per volume of pine bark, and in particular, a pulverized pine bark is used preferably. There is no particular limitation regarding the process for pulverizing the pine bark, and for example, it is possible to use the pulverizer that was employed when measuring the content of the aqueous ethanol soluble components in the pine bark. In order to increase the pulverization efficiency, the pine bark may be pulverized after the addition of water or an organic solvent such as ethanol, methanol, or ethyl acetate, to the pine bark. The size of the pulverized product is preferably 0.1 to 10 mm, and more preferably 0.1 to 5 mm.

In the extraction, as described above, at least one of water and an organic solvent can be used. Namely, water, an organic solvent, or a mixture of water and an organic solvent (hereinafter, these are collectively referred to as "extraction solvent") can be used. In view of increasing the extraction efficiency, a high extraction temperature is preferable. For example, when water is used, the extraction is performed with the use of hot water of 50 to 120° C., preferably 70 to 100° C. Hot water may be added to the pine bark. Alternatively, water is add to the pine bark and the resultant mixture can be heated. The extraction time is determined as appropriate, depending on the extraction temperature. In general, the extraction time is from 10 minutes to 24 hours.

Examples of the organic solvent include methanol, ethanol, 1-propanol, 2-propanol, 1-butanol, 2-butanol, acetone, propylene glycol, aqueous ethanol, aqueous propylene glycol, methyl ethyl ketone, glycerin, methyl acetate, ethyl acetate, 1,1,1,2-tetrafluoroethane, and 1,1,2-trichloroethene. These organic solvents can be used alone or in combination. In view of the disposal of liquid waste formed in the production process, or in view of the treatment with a synthetic resin adsorbent described later, water, ethanol, or a mixed solvent of water and ethanol (aqueous ethanol) is preferably used. When the pine bark extract that is obtained is to be concentrated further, an organic solvent such as ethanol, which has a lower boiling point than water or a mixed solvent of such an organic solvent and water, is preferably employed. Such a solvent allows the resultant pine bark extract to be concentrated at a relatively low temperature and in a relatively short time.

When the proanthocyanidin-containing product that is ultimately obtained is used as a food product or drug, then water, ethanol, and aqueous ethanol are particularly preferable in terms of safety.

The amount of the extraction solvent can be determined in view of the intended proanthocyanidin concentration and extraction efficiency. For example, when water, ethanol, or aqueous ethanol is used as the extraction solvent, the amount of extraction solvent is preferably determined to 3 to 100 parts by weight and more preferably 10 to 50 parts by weight with respect to one part by weight of the dry weight of the pine bark. Alternatively, the amount of extraction solvent is preferably 3 to 100 parts by volume and more preferably 10 to 100 parts by volume with respect to one part by weight of the dry weight of the pine bark. It should be noted that in case where water and/or an organic solvent is added to perform pulverization, the amount of the extraction solvent to be added can be determined by taking the amount of solvent used for the pulverization into account.

As the method for extraction with the use of an organic solvent, heat extraction method or supercritical fluid extraction method is preferable.

As heat extraction methods, a method of adding heated solvent to the pine bark or a method of adding the solvent to the pine bark and then heating the resultant mixture can be employed. For example, a water-ethanol mixed solvent (aqueous ethanol) comprising water and ethanol in a weight ratio of 1:1 to 1:9 is used as the extraction solvent in an amount of 1 to 20 times the weight of the pulverized pine bark. Then, the extraction is performed by stirring the resultant mixture for 0.5 to 6 hours while refluxing at 70 to 85° C. When the temperature of the extraction is not raised to the temperature of reflux, the extraction efficiency can be increased by a process including the steps of performing a heat extraction once with the mixed solvent, recovering the supernatant from the resultant mixture by filtration or the like, adding the mixed solvent to the remaining residue, and warming the resultant mixture.

Supercritical fluid extraction is a method for extracting a target component using a supercritical fluid. A supercritical fluid is in a state that is above the liquid-vapor critical point in the phase diagram showing critical temperature and critical pressure. Examples of compounds that can be employed as a supercritical fluid include carbon dioxide, ethylene, propane, and nitrous oxide (laughter gas). Carbon dioxide is preferably used.

Supercritical fluid extraction includes an extraction step in which a target component is extracted with a supercritical fluid and a separation step in which the target component is separated from the supercritical fluid. In the separation step, any separation process can be employed, examples of which include a separation based on a change in pressure, a separation based on a change in temperature, and a separation using an adsorbent or absorbent.

Moreover, it is also possible to perform supercritical fluid extraction in which an entrainer is added. In this method, supercritical fluid extraction is performed using an extracting fluid obtained by adding, for example, ethanol, propanol, n-hexane, acetone, toluene, or another aliphatic lower alcohol, aliphatic hydrocarbon, aromatic hydrocarbon, or ketone at about 2 to 20 w/v % to a supercritical fluid, so that the solubility of a target substance to be extracted, such as OPCs and catechins (described later), in the extracting fluid is dramatically increased or the selectivity of separation is enhanced. Thus, proanthocyanidins are obtained efficiently.

For extraction, any extraction apparatus, for example, a batch type, semi-continuous, or continuous extraction apparatus can be used.

As necessary, it is possible to centrifuge or filter the extract that is obtained in the extraction process in order to remove solid material or components that are not soluble in the extraction solvent. It is preferable that filtration is performed after adding a filter aid such as diatomaceous earth to the extract so that the filtration process is performed in a short time. In this case, there is no particular limitation regarding the amount of filter aid that is added, and for example, it is possible for approximately 0.001 g/mL to 0.1 g/mL diatomaceous earth to be added to the extract.

The pine bark extract that is obtained by this pre-treatment is then treated with the synthetic resin adsorbent. In the present invention, it is possible to concentrate the pine bark extract in advance of the treatment with the synthetic resin adsorbent. Concentration can remove residual organic solvent in the pine bark extract. Thus, concentration is particularly preferable if there is a possibility that the organic solvent may inhibit treatment by the synthetic resin adsorbent. When concentration is conducted, insoluble material in the pine bark extract is preferably removed in advance by filtration, for example. This allows the concentration to be conducted uniformly, and it is easy to adjust the concentration degree of the resultant concentrate.

Examples of concentration methods include methods that are ordinarily used by those skilled in the art, such as heat concentration, reduced-pressure concentration, freeze drying, concentration by ultrafiltration membrane, and concentration by dialysis membrane. Since there is little heat decomposition of proanthocyanidins and OPCs, reduced-pressure concentration, freeze drying, and concentration by ultrafiltration membrane are preferable, and reduced-pressure concentration is more preferable. These concentration methods can be employed alone or in combination.

When heat concentration is conducted, in general, heating is performed at a temperature between 40 and 100° C. in order to prevent heat decomposition of proanthocyanidins and OPCs. In the case of reduced-pressure concentration as well, it is possible to conduct the reduced-pressure concentration while heating within the above temperature range in order to conduct the concentration in a shorter time.

There is no particular limitation regarding the concentration degree of the resultant concentrate. Concentration is conducted such that the volume of the concentrate is preferably ½ to 1/100, more preferably ⅕ to 1/70, and even more preferably 1/10 to 1/50 with respect to the volume of the extract before the concentration. In particular, in view of obtaining the proanthocyanidins at a high yield, it is preferable that concentration is conducted until the organic solvent (e.g. ethanol) concentration in the pine bark extract is less than 10 volume %.

(Synthetic Resin Adsorbent Treatment Process)

By further treating the pine bark extract that is obtained through the above pre-treatment with a synthetic resin adsorbent, impurities such as saccharides and organic acids are removed. Specifically, this treatment is performed by bringing the pine bark extract and the synthetic resin adsorbent into contact with each other in order to adsorb the proanthocyanidins to the synthetic resin adsorbent, then washing with water, as necessary, and then eluting the adsorbed proanthocyanidins from the adsorbent with a predetermined solvent and recovering the resultant eluate. It should be noted that removal of insoluble material in the pine bark extract in advance is preferable in order to efficiently perform the process of treating with a synthetic resin adsorbent.

Examples of the synthetic resin adsorbent that is used in this process include organic resins, ion-exchange resins, silica gel, and silica gel used for reverse phase chromatography. It is possible for the synthetic resin adsorbent to be used alone, and, depending on the treatment method, it is also possible for a combination of two or more adsorbents to be used.

Examples of organic resins include aromatic resins, (meth) acrylic acid resins, (meth)acrylate resins, and acrylonitrile aliphatic resins. Preferable examples are aromatic resins, (meth)acrylic acid resins, and (meth)acrylate resins.

Examples of aromatic resins include a resin that is a copolymer of styrene and divinylbenzene. Specific examples of such a resin that is a copolymer of styrene and divinylbenzene include Diaion (registered trademark) HP20, Diaion HP21, Diaion HP30, Diaion HP40, and Diaion HP50, Sepabeads (registered trademark) SP800, Sepabeads SP825, Sepabeads SP850, Sepabeads SP875, Sepabeads SP70, and Sepabeads SP700 (each of the above products is manufactured by Mitsubishi Chemical Corporation), and Amberlite (registered trademark) XAD-4, Amberlite XAD-16HP, Amberlite XAD-1180, and Amberlite XAD-2000 (each of the above products is manufactured by Organo Co.).

Examples of (meth)acrylic acid resins include a resin that is a polymer of acrylic acid and a resin that is a polymer of methacrylic acid.

Examples of (meth)acrylate resins include a resin that is a polymer of acrylate and a resin that is a polymer of methacrylate. A specific example of a resin that is a polymer of acrylate includes Amberlite (registered trademark) XAD-7HP. A specific example of a resin that is a polymer of methacrylate includes Diaion (registered trademark) HP-2MG (manufactured by Mitsubishi Chemical Corporation).

Among these adsorbents, in particular, a resin that is a copolymer of styrene and divinylbenzene is preferable, and Diaion (registered trademark) HP20, Amberlite XAD-1180, and Amberlite XAD-2000 are even more preferable. In case where treatment is performed by using the resin that is a copolymer of styrene and divinylbenzene, it is preferable that the concentration is conducted so that the organic solvent in the pine bark extract is reduced to less than 10 wt % in advance. By treating such a concentrate with the above-mentioned copolymer, the proanthocyanidins may be obtained in high yield.

The amount of the synthetic resin adsorbent can be determined as appropriate in accordance with the type of the solvent and the type of the synthetic resin adsorbent or the like. For example, the synthetic resin adsorbent is preferably used in an amount of 0.01 to 50 times, and preferably 0.1 to 20 times the dry weight of the pine bark extract. When the amount of the synthetic resin adsorbent is less than 0.01 times the dry weight of the pine bark extract, the recovery of the proanthocyanidins may be low, and this is not preferable.

Among the synthetic resin adsorbents, when a synthetic resin adsorbent that has a high efficiency of adsorbing proanthocyanidins, such as Diaion (registered trademark) or Amberlite (registered trademark), is used, the amount of the adsorbent can be readily determined based on the dry weight of the raw pine bark rather than based on the dry weight of the pine bark extract. This can be possible because the adsorption efficiency of the adsorbent is good. Specifically, the amount of the synthetic resin adsorbent is determined such that the apparent swollen volume when the synthetic resin adsorbent is swollen with a solvent such as water is 0.1 mL to 5 mL, and preferably 0.5 to 3 mL, per 1 g dry weight of the pine bark. Also in this case, contact between the pine bark extract and the synthetic resin adsorbent is sufficient, and efficient adsorption can be achieved as well.

Contact between the pine bark extract and the synthetic resin adsorbent may be effected by any method. For example, some convenient methods include a column chromatography method and a batch method. The column chromatography method comprises the step of filling the synthetic resin adsorbents in a column and applying the pine bark extract on the column. The batch method comprises the step of adding the synthetic resin adsorbents to the pine bark extract, and removing the synthetic resin adsorbent after the predetermined period of time.

In treatment employing the column chromatography method, for example, first a column is filled with the synthetic resin adsorbent and the pine bark extract is applied on the column. Next, as necessary, water is applied on the column, wherein the volume of water is 0.5 to 10 times the volume of the synthetic resin adsorbent. By doing this, saccharides and organic acids that are impurities can be removed. Next, the proanthocyanidins are eluted from the synthetic resin adsorbent with the use of a solvent, and by recovering a liquid that is eluted from the synthetic resin adsorbent, it is possible to obtain proanthocyanidin-containing product with a large amount of OPCs.

Examples of the elution solvent include water, methanol, ethanol, ethyl acetate, and mixed solvents of these. In terms of safety, it is preferable that a mixed solvent of water and an alcohol (e.g. methanol or ethanol), and more preferably, a mixed solvent of water and ethanol is used.

When the mixed solvent of water and alcohol is used as the elution solvent, the mixing ratio of water and ethanol can be determined as appropriate in accordance with the synthetic resin adsorbent that is used. For example, when a copolymer of styrene and divinylbenzene is used as the synthetic resin adsorbent, an aqueous solution containing alcohol (ethanol in particular) at preferably 5 to 30 volume %, more preferably 10 to 30 volume %, even more preferably 15 to 30 volume %, and most preferably 20 to 30 volume %, is used. Setting in this way makes it possible to obtain proanthocyanidin-containing product with a yield of at least 0.01 wt %, preferably at least 0.05 wt %, and more preferably at least 0.1 wt % with respect to dry weight of pine bark. It should be noted that when the alcohol concentration is low (for example, less than 5 wt %), the OPC content of the proanthocyanidin-containing product that is obtained increases. However, it cannot be possible to sufficiently recover the adsorbate from the column, and thus the yield of the proanthocyanidin-containing product may be low. When the alcohol concentration is high (for example, larger than 30 volume %), the yield of the proanthocyanidin-containing product increases but the OPC content of the proanthocyanidin-containing product may decrease.

In treatment employing the batch method, a synthetic resin adsorbent with the same weight ratio as in the column chromatography method is added to the pine bark extract and these are bringing into contact with each other for 1 to 3 hours under stirring. Then, the adsorbent to which proanthocyanidins are adsorbed is recovered by filtration or centrifugation. The synthetic resin adsorbent is added to a solvent with the same composition as in the case of the column chromatography method, and the resultant mixture is stirred for 1 to 3 hours to release proanthocyanidins from the adsorbent. Then the supernatant is recovered by filtration or centrifugation. Thus, a proanthocyanidin-containing product containing a large amount of OPCs can be obtained.

Thus, by the process of employing a specific starting material and performing extraction of the material, followed by the treatment with a synthetic resin adsorbent, it is possible to obtain proanthocyanidin-containing product containing at least 10 wt % of OPCs.

(Proanthocyanidin-Containing Product)

The proanthocyanidin-containing product that is obtained in this way contains proanthocyanidins at a high ratio, and in particular, it contains at least 10 wt % of OPCs. Here, the term "proanthocyanidin-containing product" also includes any one or more of e.g., the concentrate, diluted product, or powder that is subsequently obtained by a process ordinarily employed by those skilled in the art.

For the proanthocyanidins in the product, proanthocyanidins having a low degree of polymerization are preferable in view of bioactivities. As the condensation products having a low degree of polymerization, condensation products having a degree of polymerization of 2 to 30 (dimer to tridecamer) are preferable, condensation products having a degree of polymerization of 2 to 10 (dimer to decamer) are more preferable, and condensation products having a degree of polymerization of 2 to 4 (dimer to tetramer) are even more preferable. In particular, the proanthocyanidin-containing product that is obtained by the production method of the present invention contains a product having a degree of polymerization of 2 to 4 (oligomeric proanthocyanidins; OPCs) at least 10 wt %, more preferably at least 20 wt %, even more preferably at least 30 wt %, yet further preferably at least 35 wt %, and most preferably at least 40 wt % in terms of dry weight.

The proanthocyanidin-containing product that is obtained in the present invention can also contain catechins preferably at 1 to 15 wt % in terms of dry weight.

The term "catechins" is a general term referring to polyhydroxyflavan-3-ols. Examples of the catechins include (+)-catechin, (−)-epicatechin, (+)-gallocatechin, (−)-epigallocatechin, epigallocatechin gallate, and epicatechin gallate.

The proanthocyanidin-containing product of the present invention can be concentrated for various applications. In order to concentrate the product, various methods such as membrane concentration, heat concentration, vacuum (reduced pressure) concentration, and freeze concentration can be employed.

Furthermore, the proanthocyanidin-containing product can be subjected to a sterilization treatment for storage as necessary. Sterilization can be performed by a method commonly used by those skilled in the art, such as high-pressure sterilization, heat sterilization, filter sterilization, and microwave sterilization.

After sterilization, the proanthocyanidin-containing product may be further concentrated, dried, and powdered. Drying is conducted by a method commonly used by those skilled in the art. In particular, freeze drying, vacuum drying, spray drying, drum drying, shelf drying, and drying by microwave are preferably used.

The proanthocyanidin-containing product that is obtained can, for example, be used as a health drink, a gelled drink and food, and the like. In addition to being used directly as a food or drink, it is also possible for the proanthocyanidin-containing product to be mixed with an excipient, an extender, a binder, a thickener, an emulsifier, a flavor, a food additive, and a seasoning, and, depending on the application, it can be formed into granule, tablet, or other forms. For example, it can be mixed with royal jelly, vitamins, protein, calcium, chitosan, lecithin, or caffeine, and furthermore, sugar solution and seasonings can be added thereto to control taste. These may be formed into capsules such as hard capsules or soft capsules, pills, or formed into a tea bag. This product can be taken as it is, depending on the form or individual preference, or may be dissolved in water, hot water, milk for drinking. In the case of the tea bag form, the components obtained by percolation may be drunk.

As described above, the proanthocyanidin-containing product that is obtained by the present invention can be widely used as a raw material of foods, cosmetics, and drugs.

EXAMPLES

Hereinafter, the present invention will be described by way of examples, but the present invention is not limited to these examples. In the examples, the abbreviation "V/V" refers to volume/volume, "W/W" refers to weight/weight, and "W/V" refers to weight/volume.

Reference Example

Preparing Pine Bark

Six types of pine bark were provided, and these were designated as pine bark A, pine bark B, pine bark C, pine bark D, pine bark E, and pine bark F, respectively. First, 2 kg of dry pine bark A was pulverized with mill to 1 to 5 mm in size in order to obtain pulverized product, and 10 g of this pulverized product was taken as a sample. To this sample was added 100 mL of aqueous solution containing 80 volume (V/V) % ethanol, and reflux extraction was performed at 80° C. for one hour. The mixture was filtrated, and a filtrate was obtained. This filtrate was designated as filtrate 1. The operation of extraction using the same type of the ethanol aqueous solution as above and filtration was performed twice on the filtration residue to obtain a filtrate (the resultant filtrates were designated as filtrates 2 and 3, respectively). The resulting filtrates 1 to 3 were combined to obtain an extraction liquid, and this was evaporated to dryness under reduced pressure in order to obtain dried product (hereinafter, this will be referred to as "aqueous ethanol soluble components"). The weight of the dried product was measured, and it was 1.32 g. Thus, it was found that the pine bark A contained the aqueous ethanol soluble components in a ratio of 13.2 wt %.

The same procedure was repeated for pine bark B and pine bark C, and the weight of the components soluble in aqueous ethanol (80 volume (V/V) %) that was obtained from 10 g of the sample was measured. For the pine bark B, it was 0.71 g, and for the pine bark C, it was 0.53 g. Therefore, it was found that the pine bark B contained the aqueous ethanol soluble components in a ratio of 7.1 wt %, and the pine bark C contained the aqueous ethanol soluble components in a ratio of 5.3 wt %.

For the pine bark D, the weight of the components soluble in aqueous ethanol (40 volume (V/V) %) that was obtained from 10 g of the sample was measured by the same procedure as described above. The result was 0.70 g. It should be noted that the weight of the components soluble in aqueous ethanol (80 volume (V/V) %) in the pine bark D was 0.66 g.

For the pine bark E, the weight of the components soluble in aqueous ethanol (30 volume (V/V) %) that was obtained from 10 g of the sample was measured by the same procedure as described above. The result was 0.35 g. It should be noted that the weight of the components soluble in aqueous ethanol (80 volume (V/V) %) in the pine bark E was 0.47 g.

For the pine bark F, the weight of the components soluble in ethanol (100 volume (V/V) %) that was obtained from 10 g of the sample was weighed by the same procedure as described above. The result was 0.72 g. It should be noted that the weight of the components soluble in aqueous ethanol (80 volume (V/V) %) in the pine bark F was 0.67 g.

Example 1

The pine bark A was used to obtain proanthocyanidin-containing product as follows.

1. Extraction Process

First, 0.5 L of water was added to 100 g of pine bark A, and reflux extraction was performed at a temperature of 95° C. or higher for one hour. Then, the mixture was filtrated and 0.5 L of filtrate was obtained (this filtrate was designated as filtrate 1). Then, by the same procedure as described above, 0.5 L of water was added to the resultant insoluble material and subjected to reflux extraction. Then, the mixture was filtrated to obtain 0.5 L of filtrate (this filtrate was designated as filtrate 2). Filtrate 1 and filtrate 2 were combined to obtain 1 L of pine bark extract liquid.

2. Synthetic Resin Adsorbent Treatment Process

Next, a column filled with resin particles made of a copolymer of styrene and divinylbenzene (Diaion (registered trademark) HP-20: manufactured by Mitsubishi Chemical Corporation) that was swollen with water to a swollen volume of 0.5 L was prepared. The extract liquid was applied on this column to adsorb the proanthocyanidins in the extract liquid to the column. The column was washed with 2 L purified water to remove saccharides, organic acids, and the like remaining in the column. Next, 1 L of aqueous solution containing 5% (V/V) of ethanol was used to elute the proanthocyanidins from the column, obtaining 1 L of a proanthocyanidin-containing liquid A. This proanthocyanidin-containing liquid A was freeze dried and its dry weight was measured and found to be 11 mg.

3. Measuring the Components in the Liquid

First, approximately 120 mg of dry powder of the proanthocyanidin-containing liquid A was obtained by repeating the process of the above-mentioned item 1 (pre-treatment process) and the above-mentioned item 2 (synthetic resin adsorbent treatment process) for ten times. Then, 100 mg of the resultant dry powder was dissolved in 2 mL ethanol, thus, obtaining a sample.

Next, this sample was fractioned into an OPC fraction, a fraction of proanthocyanidins having a degree of polymerization of 5 or more, a fraction of catechins, and a fraction of other components than catechins by using Sephadex LH-20 (manufactured by Amersham Biotech), and the content of each component was measured in the following manner.

First, 25 mL of Sephadex LH-20 (manufactured by Amersham Biotech) swollen with water was filled in a 15 mm×300 mm column, and this was washed with 50 mL of ethanol. The sample was applied on the column for adsorption. Thereafter, gradient elution was conducted using 100 to 80% (V/V) ethanol-water mixed solvents, and the resultant eluate was collected in fraction of 10 mL each. When the fractions were collected, each of the fractions was subjected to silica gel thin-layer chromatography (TLC) under the following conditions to detect whether or not OPCs were present, using specimens of dimeric to tetrameric OPCs (dimer: proanthocyanidin B-2 (Rf value: 0.6), trimer: proanthocyanidin C-1 (Rf value: 0.4), and tetramer: cinnamtannin $A_2$ (Rf value: 0.2)) as indicators.

TLC: silica gel plate (manufactured by Merck&Co., Inc.)
Eluent: benzene/ethyl formate/formic acid (2/7/1)
Detection reagent: sulfuric acid reagent and anisaldehyde sulfuric acid reagent
Amount of sample liquid: 10 μL each The eluted fractions that were confirmed to contain OPCs by TLC were combined to obtain an OPC fraction.

Next, at the point when OPCs were not detected any more, 300 mL of a 50% (V/V) water-acetone mixed solvent was applied on the column to elute the remaining adsorbates that were adsorbed to the column.

The fraction containing the collected adsorbates was subjected to TLC with catechin (Rf value: 0.8) as the indicator, and thus, divided into a fraction containing catechins and a fraction containing proanthocyanidins having a degree of polymerization of 5 or more. The developing conditions of TLC and the detection method were the same as described above.

The fraction containing catechins was further divided into a fraction containing catechins and a fraction containing other components than catechins in the following manner. First, the fraction containing catechins was freeze-dried to obtain a powder. This powder was dissolved in 3 mL of water, and the resultant solution was applied on a 15×300 mm column filled with 20 mL of MCI Gel (manufactured by Mitsubishi Chemical Corporation) swollen with water for adsorption. This column was washed with water, and then gradient elution was conducted using 10 to 100% (v/v) ethanol-water mixed solvents, and the resultant eluate was collected in fractions of 7 mL each. After the elution, TLC was conducted to detect catechins in each of the fractions using a catechin as an indicator, and thus the fractions were divided into a catechin fraction (i.e., a combined catechin fraction) and a fraction (i.e., a combined fraction) of other components than catechins.

The thus obtained OPC fraction, fraction of proanthocyanidins having a degree of polymerization of 5 or more, catechin fraction, and fraction of other components than catechins were powdered by freeze drying, and the dry weight was measured. The total of the OPC fraction, the fraction of proanthocyanidins having a degree of polymerization of 5 or more, the catechin fraction, the fraction of other components than catechins, and the fraction of other components was at least 99 mg with respect to 100 mg of the dry powder obtained from the proanthocyanidin-containing liquid A. This means that almost all the components had been recovered.

Table 1 shows the dry weight (amount of solid material) of the proanthocyanidin-containing liquid A that is obtained from 100 g of pine bark A, the content of the OPCs contained in the dry powder of the proanthocyanidin-containing liquid A, the content of proanthocyanidins having a degree of polymerization of 5 or more, the content of total proanthocyanidins (total of OPCs and proanthocyanidins having a degree of polymerization of 5 or more), the content of catechins, and the ratio of OPCs in the total proanthocyanidins.

Example 2

A proanthocyanidin-containing liquid B was obtained in the same manner as in Example 1, except that an aqueous solution containing 10% (V/V) of ethanol was used instead of an aqueous solution containing 5% (V/V) of ethanol in the synthetic resin adsorbent treatment process. The dry weight of the proanthocyanidin-containing liquid B was 55 mg. As in Example 1, 100 mg of dry powder was obtained, and the content of each component was measured with respect to this dry powder. The results also are shown in Table 1.

Example 3

A proanthocyanidin-containing liquid C was obtained in the same manner as in Example 1, except that an aqueous solution containing 20% (V/V) of ethanol was used instead of an aqueous solution containing 5% (V/V) of ethanol in the synthetic resin adsorbent treatment process. The dry weight of the proanthocyanidin-containing liquid C was 131 mg. The content of each component was measured in the same manner as in Example 1. The results also are shown in Table 1.

Example 4

A proanthocyanidin-containing liquid D was obtained in the same manner as in Example 1, except that an aqueous solution containing 30% (V/V) of ethanol was used instead of an aqueous solution containing 5% (V/V) of ethanol in the synthetic resin adsorbent treatment process. The dry weight of the proanthocyanidin-containing liquid D was 295 mg. The content of each component was measured in the same manner as in Example 1. The results also are shown in Table 1.

Example 5

A proanthocyanidin-containing liquid E was obtained in the same manner as in Example 3, except that the pine bark B (containing 7.1 wt % of aqueous ethanol (80 volume (V/V) %) soluble components) was used instead of the pine bark A. The dry weight of the proanthocyanidin-containing liquid E was 82 mg. As in Example 1, 100 mg of dry powder was obtained, and the content of each component was measured with respect to this dry powder. The results also are shown in Table 1.

Comparative Example 1

A proanthocyanidin-containing liquid F was obtained in the same manner as in Example 3, except that the pine bark C (containing 5.3 wt % of aqueous ethanol (80 volume (V/V) %) soluble components) was used instead of the pine bark A. The dry weight of the proanthocyanidin-containing liquid F was 64 mg. As in Example 1, 100 mg of dry powder was obtained, and the content of each component was measured with respect to this dry powder. The results also are shown in Table 1.

Comparative Example 2

A proanthocyanidin-containing liquid G was obtained in the same manner as in Example 3, except that the pine bark D (containing 7.0 wt % of aqueous ethanol (40 volume (V/V) %) soluble components) was used instead of the pine bark A. The dry weight of the proanthocyanidin-containing liquid G was 53 mg. As in Example 1, 100 mg of dry powder was obtained, and the content of each component was measured with respect to this dry powder. The results also are shown in Table 1.

Comparative Example 3

A proanthocyanidin-containing liquid H was obtained in the same manner as in Example 3, except that the pine bark E (containing 3.5 wt % of aqueous ethanol (30 volume (V/V) %) soluble components) was used instead of the pine bark A. The dry weight of the proanthocyanidin-containing liquid H was 45 mg. As in Example 1, 100 mg of dry powder was obtained, and the content of each component was measured with respect to this dry powder. The results also are shown in Table 1.

Comparative Example 4

A proanthocyanidin-containing liquid I was obtained in the same manner as in Example 3, except that the pine bark F (containing 7.2 wt % of ethanol (100 volume (V/V) %) soluble components) was used instead of the pine bark A. The dry weight of the proanthocyanidin-containing solution I was 50 mg. As in Example 1, 100 mg of dry powder was obtained, and the content of each component was measured with respect to this dry powder. The results also are shown in Table 1.

Comparative Example 5

Pine bark extract liquid was obtained as in Example 1 (this extract liquid is referred to as a proanthocyanidin-containing liquid J), and the amount of each component contained in this pine bark extract liquid was measured in the same manner as in Example 1. The results also are shown in Table 1.

TABLE 1

|  |  | Raw material | | Treatment process | | |
|---|---|---|---|---|---|---|
|  | Pine bark | Aqueous ethanol | Aqueous ethanol soluble components (wt %) | Extraction process | Adsorbent[*1] treatment process (elution solvent) | Pro[*2] containing liquid |
| Ex. 1 | A | 80% (V/V) EtOH Aq.[*4] | 13.2 | Done | 5% (V/V) EtOH Aq.[*4] | A |
| 2 | A | 80% (V/V) EtOH Aq.[*4] | 13.2 | Done | 10% (V/V) EtOH Aq.[*4] | B |
| 3 | A | 80% (V/V) EtOH Aq.[*4] | 13.2 | Done | 20% (V/V) EtOH Aq.[*4] | C |
| 4 | A | 80% (V/V) EtOH Aq.[*4] | 13.2 | Done | 30% (V/V) EtOH Aq.[*4] | D |
| 5 | B | 80% (V/V) EtOH Aq.[*4] | 7.1 | Done | 20% (V/V) EtOH Aq.[*4] | E |
| Con. Ex. 1 | C | 80% (V/V) EtOH Aq.[*4] | 5.3 | Done | 20% (V/V) EtOH Aq.[*4] | F |
| 2 | D | 40% (V/V) EtOH Aq.[*4] | 7.0 | Done | 20% (V/V) EtOH Aq.[*4] | G |
| 3 | E | 30% (V/V) EtOH Aq.[*4] | 3.5 | Done | 20% (V/V) EtOH Aq.[*4] | H |

TABLE 1-continued

| | | | | | | |
|---|---|---|---|---|---|---|
| 4 | F | 100% (V/V) EtOH | 7.2 | Done | 20% (V/V) EtOH Aq.*4 | I |
| 5 | A | 80% (V/V) EtOH Aq.*4 | 13.2 | Done | No treatment | J |

| | | Measurement results | | | | |
|---|---|---|---|---|---|---|
| | | | Proanthocyanidins | | | |
| | | Weight of solid material (mg/100 g of pine bark) | Content of OPCs (% W/W) | Content of 5-mer or more (% W/W) | Content of total pro*2 (% W/W) | OPC/ total pro*3 | Catechins Content of catechins (% W/W) |
| Ex. | 1 | 11 | 73.3 | 8.3 | 81.7 | 89.8 | 16.7 |
| | 2 | 55 | 66.9 | 14.8 | 81.7 | 81.9 | 13.8 |
| | 3 | 131 | 40.3 | 40.0 | 80.3 | 50.2 | 9.6 |
| | 4 | 295 | 22.1 | 60.1 | 82.2 | 26.9 | 5.0 |
| | 5 | 82 | 11.9 | 54.4 | 66.3 | 17.9 | 6.1 |
| Con. | 1 | 64 | 8.3 | 42.5 | 50.8 | 16.3 | 5.2 |
| Ex. | 2 | 53 | 7.3 | 37.2 | 44.7 | 16.8 | 4.5 |
| | 3 | 45 | 6.7 | 32.5 | 39.2 | 17.1 | 4.2 |
| | 4 | 50 | 7.2 | 35.3 | 42.5 | 16.8 | 4.3 |
| | 5 | 12890 | 1.2 | 9.9 | 14.9 | 33.4 | 0.3 |

*1 Synthetic resin adsorbent
*2 Proanthocyanidin (s)
*3 (Content of OPCs)/(content of total proanthocyanidins) × 100
*4 Aqueous ethanol solution From the results of Table 1, it can be understood that each of the proanthocyanidin-containing liquids A to E of Examples 1 to 5, which was obtained by subjecting the pine bark A or the pine bark B to hot water extraction treatment and synthetic resin adsorbent treatment, contains at least 10 wt % of OPCs. This demonstrates that proanthocyanidin-containing product containing at least 10 wt % of OPCs is readily obtained by performing extraction and synthetic resin adsorbent treatment using a pine bark as the starting material, wherein the pine bark has characteristics in that at least 7 wt % of solid material in terms of dry weight is obtained from a pine bark extract that is obtained by adding 10 parts by volume of an aqueous ethanol solution containing ethanol in the range of 50 to 80 volume % to one part by weight of the pine bark, and performing extraction at 80 to 85° C. for one hour.

It can be understood from Examples 1 to 4 that in the process of the treatment with a synthetic resin adsorbent, there is a tendency as follows: the lower the ethanol concentration in the elution solvent is, the higher the OPC content is and the lower the yield of the resultant product is. Conversely, it is also evident that there is a tendency for the yield from the pine bark to increase as the ethanol concentration becomes higher.

On the other hand, in each of the proanthocyanidin-containing liquids F to I of Comparative Examples 1 to 4 that was obtained by using one of the pine barks C to F and in the proanthocyanidin-containing liquid J of Comparative Example 5 that was obtained by performing only the extraction treatment on the pine bark A, the OPC content was less than 10 wt %. With regard to the pine bark D and the pine bark F in particular, even though the content of the soluble components was at least 7 wt % when the aqueous ethanol solution containing ethanol in the range of 40 volume % or 100 volume % ethanol, which are solvents that can extract OPCs, was used, it was not possible to obtain a proanthocyanidin-containing product that contains at least 10 wt % of OPCs.

Example 6

First, 1 L of purified water was added to 100 g of the pine bark A of the reference example, and the pine bark A was pulverized and heated at 100° C. for 10 minutes. Then, the mixture was then immediately filtrated and the resultant insoluble material was washed with 200 mL of purified water. The filtrate and the washing liquid were combined to obtain 1.2 L of extraction liquid.

Next, this extraction liquid was cooled to 25° C. and 100 g of Diaion (registered trademark) HP-20 was added thereto and the mixture was stirred for three hours. Thereafter, the mixture was filtrated to obtain a solid material to which proanthocyanidins have been adsorbed. This solid material was washed with 400 mL of purified water and 200 mL of 20% (V/V) aqueous ethanol solution was added, and the mixture was stirred for one hour. Thereafter, the mixture was filtrated to obtain a proanthocyanidin-containing liquid (this liquid was designated as proanthocyanidin-containing liquid K). The proanthocyanidin-containing liquid K was evaporated to dryness under reduced pressure to obtain 0.13 g of dry powder. With respect to 100 mg dry powder of the proanthocyanidin-containing liquid K, the OPC content and the catechin content were measured in the same manner as in Example 1. The OPC content was 41.1 wt % and the catechin content was 10.1 wt % in terms of dry weight.

Example 7

A proanthocyanidin-containing liquid L was obtained in the same manner as Example 1, except that Amberlite (registered trademark) XAD1180 was used instead of the synthetic resin adsorbent (Diaion (registered trademark) HP-20) employed in Example 1. The proanthocyanidin-containing liquid L was evaporated to dryness under reduced pressure to obtain 0.07 g of dry powder. As in Example 1, 100 mg of dry powder was obtained, and the OPC content and the catechin content were measured with respect to this dry powder. The OPC content was 38.2 wt % and the catechin content was 9.2 wt % in terms of dry weight.

Example 8

A proanthocyanidin-containing liquid M was obtained in the same manner as Example 1, except that Amberlite (registered trademark) XAD2000 was used instead of the synthetic resin adsorbent (Diaion (registered trademark) HP-20) of Example 1. The proanthocyanidin-containing liquid M was evaporated to dryness under reduced pressure to obtain 0.13 g of dry powder. Using 100 mg of the dry powder of the proanthocyanidin-containing liquid M, the OPC content and the catechin content were measured in the same manner as in Example 1. The OPC content was 40.2 wt % and the catechin content was 10.2 wt % in terms of dry weight.

INDUSTRIAL APPLICABILITY

According to the method of the present invention, it is possible to conveniently and efficiently obtain proanthocyanidin-containing product that contains at least 10 wt % of OPCs by the process of providing a pine bark as a starting material, extracting the pine bark with at least one of water and an organic solvent, and treating the resultant extract with a synthetic resin adsorbent, wherein the pine bark has characteristics in that at least 7 wt % of solid material in terms of dry weight is obtained from a pine bark extract that is obtained by adding 10 parts by volume of an aqueous ethanol solution containing ethanol in the range of 50 to 80 volume % to one part by weight of the pine bark, and performing extraction at 80 to 85° C. for one hour. This method is particularly useful in terms of cost and environmental safety. The resultant proanthocyanidin-containing product that contains at least 10 wt % of OPCs may also contain catechins. The proanthocyanidin-containing product is very useful as a raw material for producing food products, cosmetics, and drugs.

The invention claimed is:

1. A method for producing proanthocyanidin-containing product, comprising the steps of:
    selecting a pine bark by adding 10 parts by volume of an aqueous ethanol solution containing ethanol in an amount of 80 volume % to one part by weight of the pine bark, performing extraction at 80° C. for one hour to obtain a filtrate, further performing the same extraction to the filtration residue twice using fresh aqueous ethanol solution to obtain filtrates, combining the filtrates to obtain the extraction liquid, evaporating the extraction liquid to dryness under reduced pressure to obtain solid material, and measuring the dry weight of the solid material;
    and after finding by said procedure that said pine bark has provided at least 7 weight % of solid material in terms of dry weight
    extracting the selected pine bark with water;
    bringing the pine bark extract and a synthetic resin adsorbent into contact with each other, wherein the synthetic resin adsorbent is selected from the group consisting of aromatic resins, (meth)acrylic acid resins, and (meth)acrylate resins;
    washing the synthetic resin adsorbent with water;
    eluting the adsorbed material from the adsorbent with an aqueous solution containing alcohol in a ratio of 10 to 30 volume %, and
    recovering the resultant eluate.

* * * * *